US009848615B2

(12) United States Patent
Bisgaard-Frantzen et al.

(10) Patent No.: US 9,848,615 B2
(45) Date of Patent: *Dec. 26, 2017

(54) STORAGE STABLE FROZEN LACTIC ACID BACTERIA CULTURE (71) Applicant: CHR. HANSEN A/S, Hørsholm (DK)

(72) Inventors: Hans Bisgaard-Frantzen, Rødovre (DK); Børge Windel Kringelum, Ballerup (DK); Inge Knap, Farum (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/587,953

(22) Filed: Dec. 31, 2014

(65) Prior Publication Data

US 2015/0223480 A1    Aug. 13, 2015

Related U.S. Application Data (63) Continuation of application No. 10/543,240, filed as application No. PCT/DK2004/000025 on Jan. 19, 2004, now abandoned.

(30) Foreign Application Priority Data

Jan. 22, 2003 (EP) .................................... 03001442

(51) Int. Cl.
*A23C 9/123* (2006.01)
*C12N 1/00* (2006.01)
*C12N 1/04* (2006.01)
*C12N 1/20* (2006.01)

(52) U.S. Cl.
CPC ................ *A23C 9/123* (2013.01); *C12N 1/00* (2013.01); *C12N 1/04* (2013.01); *C12N 1/20* (2013.01); *A23Y 2220/03* (2013.01); *A23Y 2240/21* (2013.01); *A23Y 2240/25* (2013.01); *A23Y 2240/41* (2013.01); *A23Y 2260/25* (2013.01); *A23Y 2260/35* (2013.01)

(58) Field of Classification Search
CPC ... C12N 1/04; C12N 1/20; C12N 1/38; C12N 15/8205; C12N 15/8207; C12N 1/00; C12N 9/1051; C12N 15/746; C12N 15/86; C12N 9/0004; C12N 9/0069; C12N 9/0071; C12N 9/16; C12N 9/2417; C12N 9/2437; A61K 35/74; A61K 35/741; A61K 35/742; A61K 39/02; A61K 9/0014; A61K 33/00; A61K 33/24; A61K 33/38; A61K 2800/24; A61K 2800/805; A61K 2800/84; A61K 35/54; A61K 35/57; A61K 35/60; A61K 35/655; A61K 35/745; A61K 35/747; A23C 17/02; A23C 19/032; A23C 9/123; A23C 15/123; A23C 19/0323; A01H 4/005; A01N 2300/00; A01N 25/00; A01N 35/02
See application file for complete search history.

(56) References Cited

U.S. PATENT DOCUMENTS

| 4,140,800 A | 2/1979 | Kline |
| 4,262,023 A | 4/1981 | Eddy et al. |
| 5,637,494 A | 6/1997 | King |
| 5,677,166 A | 10/1997 | Broadbent et al. |
| 5,919,695 A | 7/1999 | Vedamuthu et al. |
| 8,481,027 B2 | 7/2013 | Stavnsbjerg et al. |
| 2002/0031527 A1 | 3/2002 | Wu et al. |
| 2002/0054936 A1 | 5/2002 | Hoier et al. |
| 2006/0204484 A1 | 9/2006 | Bisgaard-Frantzen et al. |
| 2007/0254353 A1 | 11/2007 | Stavnsbjerg et al. |

FOREIGN PATENT DOCUMENTS

| DE | 28 05 676 | 8/1978 |
| EP | 0 259 739 | 3/1988 |
| EP | 0 259 739 A1 | 3/1988 |
| EP | 1 441 027 | 7/2004 |
| FR | 2393251 | 12/1978 |
| NL | 7205909 | 11/1973 |
| WO | WO-91/11509 | 8/1991 |
| WO | WO-00/39281 | 7/2000 |
| WO | WO-2004/065584 | 8/2004 |

OTHER PUBLICATIONS

F.J. Chavarri et al., "Cryoprotective Agents for Frozen Concentrated Starters From Non-Bitter *Streptococcus lactis* Strains", Biotechnology Letters, vol. 10, No. 1, 11-16, Jan. 1988.
Fernando Fonseca et al., "Operating Conditions That Affect the Resistance of Lactic Acid Bacteria to Freezing and Frozen Storage", Cryobiology 43, 189-198, Nov. 2001.
Final Office Action issued in U.S. Appl. No. 12/837,217 dated Jan. 15, 2013.
Final Office Action issued in U.S. Appl. No. 10/543,240 dated Oct. 13, 2010.
Food Chemistry Third Edition, edited by Owen R. Fennema, University of Wisconsin, Madison, WI, pp. 55-87, 1996.
International IDF Standard 146a:1998, Yoghurt: Identification of Characteristic Microorganisms (*Lactobacillus delbrueckii* subsp. *Bulgaricus* and *Streptococcus thermophilus*), IDF General Secretariat, Dec. 1998, pp. 1-6.
International Search Report dated Jun. 4, 2004 for PCT Application No. PCT/DK2004/000025.
Non-Final Office Action issued in U.S. Appl. No. 10/543,240 dated Oct. 17, 2011.
Non-Final Office Action issued in U.S. Appl. No. 10/543,240 dated Aug. 20, 2008.
Non-Final Office Action issued in U.S. Appl. No. 10/543,240 dated Feb. 18, 2009.

(Continued)

*Primary Examiner* — Debbie K Ware
(74) *Attorney, Agent, or Firm* — Foley & Lardner LLP (57) ABSTRACT A storage stable frozen lactic acid bacteria (LAB) culture that comprises LAB that are that are able to utilize sucrose, has a weight of at least 50 g frozen material and a content of viable bacteria of at least $10^9$ colony forming units (CFU) per g frozen material.

19 Claims, 11 Drawing Sheets (56) References Cited

OTHER PUBLICATIONS

Non-Final Office Action issued in U.S. Appl. No. 10/543,240 dated Nov. 25, 2009.
Non-Final Office Action issued in U.S. Appl. No. 10/590,153 dated Oct. 5, 2009.
Non-Office Action issued in U.S. Appl. No. 10/590,153 dated Feb. 18, 2010.
Non-Office Action issued in U.S. Appl. No. 12/837,217 dated Jun. 13, 2012.
Notice of Allowance issued in U.S. Appl. No. 12/837,217 dated Mar. 7, 2013.
Paul B. Conrad et al., "Stabilization and Preservation of *Lactobacillus acidophilus* in Saccharide Matrices", Cryobiology, 41: 17-24, Aug. 2000.
R. Carcoba et al., "Influence of cryoprotectants on the viability and acidifying activity of frozen and freeze-dried cells of the novel starter strain *Lactococcus lactis* ssp. *lactis* CECT 5180", Eur Food Res Technol, 211: 433-437, Nov. 2000.
Roos et al., A Research Note Phase Transitions of Amorphous Sucrose and Frozen Sucrose Solutions, Journal of Food Science, vol. 56(1): 266-67, Jan. 1991.
Roos, Phase Transitions in Foods, Food science and technology, Oct. 9, 2002, pp. 99-101.
Search Report dated Mar. 13, 2003 for EP Application No. 03001442.
CesKa® -stAr D 507 invoice including Annexes dated Nov. 11, 2002, 13 pages.
Daly, "The use of mesophilic cultures in the dairy industry", Antonie van Leeuwenhoek, 49:297-312, May 1983, 16 pages.
de Roissart, Bactéries Lactiques, vol. 1, ISBN: 2-9507477-0-1, Jan. 1994, pp. 70-71, 74, 80, 82, 85.
Jabarit, "Influence de la congélation et de la cryo-dessiccation sur le taux de survie et le pourcentage des ferments lactiques dans le bioghurt", Le Lait No. 488, pp. 520-532 Sep./Oct. 1969.
Letter of the applicant in examination procedure of the Opposed Patent dated Oct. 16, 2012, 7 pages.
Mayra-Makinen and Bigret, "Mesophilic and Thermophilic Starters Used by Dairy Industry", in: Salminen and von Wright: Lactic Acid Bacteria, Second Edition, Published by Marcel Dekker, Inc., 1998, p. 74.
Nazzaro et al., "Effect of Added Carbohydrates on Survival of Some Dried Lactic Acid Bacteria", Med. Fac. Landbouww, Univ. Gent. 64/5a, pp. 253-258, Sep. 1999.
Nizostar I233 Product specification dated Aug. 12, 1999, including Annexes dated Apr. 25, 2002, 6 pages.
Roos, "Phase transitions in foods", Published by Academic Press Limited, 1995, ISBN: 0-12-595340-2, p. 116.
Smit et al., "Screening for and Control of Debittering Properties of Cheese Cultures", in: Flavour Science: Recent Developments, eds. A.J. Taylor and D.S. Mottram, The Royal Society of Chemistry, 1996, pp. 25-31.
Stadhouders et al., "A study of the optimum conditions of freezing and storing concentrated mesophilic starters", Neth. Milk Diary J., 25:229-239, 1971.
Stadhouders et al., "Preservation of starters and mass production of starter bacteria", Neth. Milk Diary J., 2:182-199, 1969.
Stadhouders, "Diary starter cultures", Milchwissenschaft, 29:329-337, Jun. 1974.
A summary of pellets allegedly sold to the public by CSK, dated 2002, 1 page.
CSK Food Enrichment, Product information sheet for CesKa-stAr dated Oct. 18, 2002, 2 pages.
CSK Food Enrichment, Product specifications of D507 (Feb. 2002) and Nizostar 500MT (Dec. 2001) from CSK Food Enrichment, 3 pages.
LD culture C 57 invoice, including Annexes dated Nov. 13, 2002, 6 pages.
Safety Data Sheet for CesKa-StAr dated Mar. 1, 2006, 7 pages.

STORAGE STABLE FROZEN LACTIC ACID BACTERIA CULTURE

FIELD OF THE INVENTION

The present invention relates to a storage stable frozen lactic acid bacteria (LAB) culture that comprises LAB that are that are able to utilize sucrose, has a weight of at least 50 g frozen material and a content of viable bacteria of at least $10^9$ colony forming units (CFU) per g frozen material.

BACKGROUND OF THE INVENTION

Microorganisms are involved in the manufacture of food and feed products including most dairy products. Thus, bacterial cultures, in particular cultures of bacteria that are generally classified as lactic acid bacteria are essential in the making of all fermented milk products, cheese and butter. Cultures of such bacteria may be referred to as starter cultures and they impart specific features to various dairy products by performing a number of functions.

Commercial dairy starter cultures are generally composed of lactic acid and citric acid fermenting lactic acid bacteria. In the present context, the expression "lactic acid bacteria" designates a group of Gram positive, catalase negative, non-motile, microaerophilic or anaerobic bacteria which ferment sugar with the production of acids including lactic acid as the predominantly produced acid, acetic acid, formic acid and propionic acid. The industrially most useful lactic acid bacteria are found among *Lactococcus* species, *Streptococcus* species, *Enterococcus* species, *Lactobacillus* species, *Leuconostoc* species and *Pediococcus* species.

Commonly used dairy starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis* subsp. *lactis*, *Lactococcus lactis* subsp. *cremoris*, *Leuconostoc mesenteroides* subsp. *cremoris*, *Pediococcus pentosaceus*, *Lactococcus lactis* subsp. *lactis* biovar. *diacetylactis* and *Lactobacillus casei* subsp. *casei*. Thermophilic lactic acid bacterial species include as examples *Streptococcus thermophilus*, *Enterococcus faecium*, *Lactobacillus lactis*, *Lactobacillus helveticus*, *Lactobacillus delbrueckii* subsp. *bulgaricus* and *Lactobacillus acidophilus*.

The dairy starter cultures are also classified according to their specific species composition and preferred industrial use. A pure starter culture comprises only a single specie and a mixed culture comprises two or more different species. Commercial relevant mesophilic mixed cultures include:

"O-culture" comprising *Lactococcus lactis* subsp. *lactis* and *Lactococcus lactis* subsp. *cremoris*.

"D-culture" comprising *Lactococcus lactis* subsp. *lactis*, *Lactococcus lactis* subsp. *cremoris* and *Lactococcus lactis* subsp. *lactis* biovar. *diacetylactis*.

"L-culture" comprising *Lactococcus lactis* subsp. *lactis*, *Lactococcus lactis* subsp. *cremoris* and *Leuconostoc mesenteroides* subsp. *cremoris*.

"LD-culture" comprising *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

An O-culture is used to make cheese without holes (Cheddar, Cheshire, Feta). A D-culture is used to make butter. A L-culture is used to cheese with only small holes (cottage cheese) and curdled milk products with low $CO_2$-production. A LD-culture is used to make cheese with normal hole sizes, curdled milk products (junket) and sour butter. Commercially, a LD-culture is currently one of the most used mixed cultures.

Commercial relevant thermophilic mixed cultures include:

"Yoghurt culture" comprising *Streptococcus thermophilus* and *Lactobacillus delbrueckii* subsp. *bulgaricus*.

"Thermophil cheese culture" comprising *Streptococcus thermophilus* and *Lactobacillus helveticus*.

An Yoghurt culture is used to make yoghurt and special Italian cheeses. An Thermophil cheese culture is used to make emmentaler cheese and special Italian cheeses.

Commercial starter cultures may commonly be distributed as frozen cultures. Highly concentrated frozen cultures are commercially very interesting since such cultures can be inoculated directly into milk without intermediate transfer. In others words, such highly concentrated frozen cultures comprises so many bacteria that dairies do not have to make in-house bulk starters. A "bulk starter" is defined herein as a starter culture propagated at the dairy plant for inoculation into milk. Highly concentrated cultures may be referred to as direct vat set (DVS)-cultures.

In order to comprise sufficient bacteria a commercial relevant highly concentrated frozen culture generally has a weight of at least 50 g and a content of viable bacteria of at least $10^9$ colony forming units (CFU) per g.

Another presentation of commercial highly concentrated DVS-starter cultures is as freeze-dried or lyophilized cultures in the form of a powder. In this form, the starter can be shipped without refrigeration.

The article of F. J. Chavarri et al (Biotechnology letters, vol 10, 1, 11-16 (1988), "Cryoprotective agents for frozen concentrated starters from non-bitter *Streptococcus Lactis* strains") describes that the storage viability of a frozen pure *Streptococcus lactis* culture could be improved by addition of 5% lactose or 5% sucrose. The lactose or sucrose worked as cryoprotective agents. *Streptococcus lactis* is a former name of *Lactococcus lactis* subsp. *lactis*.

Similarly, the article of R. Cárcoba et al (Eur Food Res Technol (2000) 211, 433-437, "Influence of cryoprotectants on the viability and acidifying activity of frozen and freeze-dried cells of the novel starter strain *Lactococcus lactis* subsp. *lactis* CECT 5180") describes that the storage viability of a frozen pure *Lactococcus lactis* subsp. *lactis* culture could be improved by addition of different cryoprotective agents such as sugars (lactose, sucrose and trehalose), glutamic acid and gelatin.

The present inventors are not aware of any commercial available highly concentrated frozen cultures that comprise significant amounts of cryoprotective agents.

EP259739 describes different suitable cryoprotective agents for freeze-dried cultures. A freeze-dried culture in the form of a powder is physically significant different from a frozen culture among others due to that a freeze-dried powder comprises significant less water as compared to a frozen culture. Accordingly, it is submitted that the skilled person would prima facie not consider that a specific cryoprotective agent described as useful for a freeze-dried culture would also be similar useful in a frozen culture.

WO00/39281 (Chr. Hansen A/S) describes a liquid starter culture stabilized by different cryoprotective agents. Page 5, lines 5-7 reads "the expression "liquid starter culture" relates to non-frozen liquid starter cultures having a liquid phase, e.g. an aqueous phase, content that is typically in the range of 50-90% by weight". Consequently, the liquid culture described in WO00/39281 is a non-frozen culture.

SUMMARY OF THE INVENTION

Prior to the present invention, the present inventors believed that there were no significant storage stability problems in relation to commercially relevant highly concentrated frozen lactic acid bacteria cultures. As said above, the present inventors are not aware of any commercial available highly concentrated frozen cultures that comprise significant amounts of cryoprotective agents.

Prior to the present invention, stability studies had been made starting from commercial highly concentrated lactic acid bacteria cultures that already had been frozen for 2-3 month. For instance, studies were made on 2-3 month old frozen LD-cultures. These studies showed no significant degradation of activity of the LD-cultures over a period of one year at temperature below −45° C. Consequently, it was believed that commercial relevant LD-cultures did not have significant storage stability problems.

In order to analyze the stability during the first weeks of frozen storage different O-cultures were analyzed right from the first day of frozen storage. They did not show any significant reduction of activity neither during the first weeks nor during the next 12 month. Accordingly, these data essentially confirmed that there should be no storage stability problems in relation to commercially relevant highly concentrated frozen cultures.

Despite this, the present inventors continued to investigate stability issues of different commercial relevant frozen cultures and after a number of studies they identified that for instance frozen LD-cultures had a significant loss of activity within the first 1-3 weeks of frozen storage. After these weeks the further loss of activity was relatively insignificant in line with the prior known results described above.

In summary, the work of the present inventors has identified hitherto unrecognized storage stability problems in relation to some types of commercial relevant highly concentrated frozen lactic acid bacteria cultures, such as e.g. commercial available frozen LD-cultures.

Once having identified this problem, the present inventors could start to try to solve the problem. As described herein they solved this by addition of cryoprotective agents to the relevant highly concentrated frozen cultures.

As said above an O-culture comprises *Lactococcus lactis* subsp. *lactis* and *Lactococcus lactis* subsp. *cremoris* and a LD-culture comprises *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

The *leuconostoc mesenteroides* subsp. *cremoris* present in the LD-culture is able to utilize sucrose. The O-culture does not comprise bacteria that are able to utilize sucrose.

Consequently, without being limited to theory, it is believed that the herein identified stability problems relate to commercial relevant highly frozen cultures that comprise bacteria that are able to utilize sucrose.

As said above, in order to comprise sufficient bacteria a commercial relevant highly concentrated frozen culture generally has a weight of at least 50 g and a content of viable bacteria of at least $10^9$ colony forming units (CFU) per g. The pure *Lactococcus lactis* subsp. *lactis* cultures described in the articles of F. J. Chavarri et al and R. Carboba et al (see above) are in the present context not considered commercial relevant highly concentrated frozen cultures since they are made on must smaller scale and comprises significant less grams of frozen culture.

Accordingly, a first aspect of the invention relates to a frozen lactic acid bacteria (LAB) culture that comprises LAB that are that are able to utilize sucrose, has a weight of at least 50 g frozen material and a content of viable bacteria of at least $10^9$ colony forming units (CFU) per g frozen material, characterized in that the frozen culture comprises from 0.5% to 80% of a cryoprotective agent measured as w/w of the frozen material.

The cryoprotective agent should preferably be added to the viable bacteria before they are frozen.

Accordingly, in a second aspect the invention relates to a method for making a frozen lactic acid bacteria (LAB) culture that comprises LAB that are that are able to utilize sucrose, has a weight of at least 50 g frozen material and a content of viable bacteria of at least $10^9$ colony forming units (CFU) per g frozen material comprising following steps:

(i) adding a cryoprotective agent to viable bacteria to get at least 50 g of material with a content of viable bacteria of at least $10^9$ colony forming units (CFU) per g material and comprising the cryoprotective agent in an amount from 0.5% to 80% measured as w/w of the material, (ii) freezing the material to get frozen material, and (iii) packing the frozen material in a suitable way.

A third aspect of the invention relates to a frozen lactic acid bacteria (LAB) culture obtainable by the method for making a frozen lactic acid bacteria (LAB) culture of the second aspects of the invention.

A fourth aspect of the invention relates to use of the frozen lactic acid bacteria (LAB) culture as described above in a process for making a food or feed product.

Definitions

Prior to a discussion of the detailed embodiments of the invention is provided a definition of specific terms related to the main aspects of the invention.

The term "LAB that are that are able to utilize sucrose" denotes LAB that are able to ferment the sugar sucrose with the production of acids.

The term "material" of the culture denotes the relevant substances of the culture including both the viable bacteria and cryoprotective agent. Possible packing is not included. Consequently, the weight of the material of the culture is not including the weight of possible packing.

The term "packing" should be understood broadly. It denotes that the frozen lactic acid bacteria (LAB) culture should be packed in order could to be provided to the user. It may be packed in a bottle, a tetra-pack, etc.

The term "a cryoprotective agent" denotes a substance that is able to improve the storage stability of the frozen culture. In the present context it may be a single specific cryoprotective agents or it may be two or more different agents. Accordingly, the w/w percentage of the cryoprotective agent(s) within the culture material should be understood as the sum of the amount of cryoprotective agent(s). A preferred way to determine whether a substance is a cryoprotective agent that is able to improve the storage stability of the frozen culture is to spilt a culture, as described herein, in two samples, add a specified amount of the cryoprotective agent to one of them, freezing both of them and measure the milk acidifying activity of the cultures on the same day as freezing and periodically up to one year under frozen storage. If the culture with cryoprotective agent has improved milk acidifying activity seen over the storage period the substance is a cryoprotective agent. A suitable milk acidifying activity assay is given in working examples herein.

Embodiments of the present invention is described below, by way of examples only

DETAILED DESCRIPTION OF THE INVENTION

A Frozen Lactic Acid Bacteria (LAB) Culture

The term "mixed lactic acid bacteria (LAB) culture" denotes a mixed culture that comprises two or more different LAB species. The term a "pure lactic acid bacteria (LAB) culture" denotes a pure culture that comprises only a single LAB species specie.

The culture as described herein may be a mesophilic culture consisting of mesophilic bacteria having optimum growth temperatures at about 30° C.

The culture as described herein comprises LAB that are that are able to utilize sucrose. The *Leuconostoc mesenteroides* subsp. *cremoris* is able to utilize sucrose. Among others, it is present in a L-culture and a LD-culture.

Consequently, in a preferred embodiment the frozen culture is a L-culture or more preferably a LD-culture. A L-culture and a LD-culture are examples of mesophilic cultures. Further they are mixed cultures. Consequently, a culture as described herein is preferably a mixed culture, more preferably a mesophilic mixed culture.

A L-culture comprises *Lactococcus lactis* subsp. *lactis*, *Lactococcus lactis* subsp. *cremoris* and *Leuconostoc mesenteroides* subsp. *cremoris*.

A LD-culture comprises *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

The specific amount of the individual bacterial species may vary in accordance with the specific required use. The skilled person is aware of this and capable of determining the preferred mixed culture composition according to the required needs.

For instance, if aroma is required a relatively high percentage of the aroma making bacteria *Lactococcus lactis* subsp. *lactis* biovar. *diacetylactis* and *Leuconostoc mesenteroides* subsp. *cremoris* could be preferred.

A preferred LD-culture comprises:

| | |
|---|---|
| *Lactococcus lactis* subsp. *lactis*, | 60-95%, |
| *Lactococcus lactis* subsp. *cremoris* | preferably 70-90% |
| *Lactococcus lactis* subsp. *lactis* biovar. | 5-40%, |
| diacetylactis, *Leuconostoc mesenteroides* subsp. *cremoris* | preferably 10 to 30% |

Within the ranges above, it is preferred to have from 0.25 to 6% of *Leuconostoc mesenteroides* subsp. *cremoris* and from 7 to 30% of *Lactococcus lactis* subsp. *lactis* biovar. *diacetylactis*.

Of course the total percentage sum of the 4 different LAB specifies cannot exceed 100%. However, it may be less than 100% if other bacteria than the 4 mentioned ones are present in the LD-culture. Working examples 1 and 2 herein provides examples of stabilized LD-cultures.

The culture as described herein may be a thermophilic culture consisting of thermophilic bacteria having optimum growth temperatures in the range of about 40 to about 45° C.

The culture as described herein comprises LAB that are that are able to utilize sucrose. The thermophilic *Lactobacillus acidophilus* is able to utilize sucrose. Accordingly, in a preferred embodiment the frozen culture is a culture comprising *Lactobacillus acidophilus*, preferably a pure *Lactobacillus acidophilus* culture. Working example 4 herein gives an example of a stabilized pure *Lactobacillus acidophilus* culture.

The thermophilic *Streptococcus thermophilus* is able to utilize sucrose. Accordingly, in a preferred embodiment the frozen culture is a mixed "Yoghurt culture" comprising *Streptococcus thermophilus* and *Lactobacillus delbrueckii* subsp. *bulgaricus*; or "Thermophil cheese culture" comprising *Streptococcus thermophilus* and *Lactobacillus helveticus*.

Highly Concentrated Frozen Lactic Acid Bacteria Cultures

The frozen cultures as described herein are, what in the food industry may be termed, highly concentrated frozen lactic acid bacteria cultures. In order to comprise sufficient bacteria such cultures should be relatively big (have a sufficient weight) combined with a relatively high concentration of viable bacteria. It is obvious that if relatively more bacteria is required the weight and/or the concentration of viable bacteria should be increased.

Preferably, a frozen lactic acid bacteria (LAB) culture as described herein has a weight of at least 100 g frozen material, more preferably a weight of at least 250 g frozen material, even more preferably a weight of at least 500 g frozen material and most preferably a weight of at least 900 g frozen material. Preferably, the weight of the frozen material is less than 500 kg.

Preferably, a frozen lactic acid bacteria (LAB) culture as described herein has a content of viable bacteria of at least $5 \times 10^9$ colony forming units (CFU) per g frozen material, more preferably a content of viable bacteria of at least $10^{10}$ colony forming units (CFU) per g frozen material, and most preferably a content of viable bacteria of at least $2 \times 10^{10}$ colony forming units (CFU) per g frozen material.

Fermentation and suitable fermentations media for LAB are known in the art and the skilled person is capable of selecting a suitable media and fermentation conditions in relation to the specific LAB. Suitable media and fermentations are given in the working example section herein.

In order to get sufficient amount of bacteria, it is in the present context preferred to make a relatively large-scale fermentation in suitable big fermentation tanks. Fermentation tanks of at least 50 l, preferably at least 90 l or bigger are preferred.

After a suitable fermentation, the viable bacteria are preferably isolated by removal of the liquid (supernatant) of the fermentation media (e.g. by centrifugation). The isolated viable bacteria may be termed the isolated biomass. The isolated viable bacteria shall preferably have a content of viable bacteria of at least $10^9$ colony forming units (CFU) per g or ml.

The frozen culture may be packaged is a suitable way in order to be provided to the user.

Preferably the frozen culture is stored at a temperature from −18° C. to −60° C., more preferably from −18° C. to −50° C. The frozen culture may be stored at a temperature from −18° C. to −25° C. The freezing of the culture shall preferably be done rapidly e.g. by freezing in liquid nitrogen.

Cryoprotective Agent

The cryoprotective agent may preferably be selected from proteins, protein hydrolysates and amino acids. Preferred suitable examples of these include the ones selected from the group consisting of Glutamic acid, Lysine, Na-glutamate, Na-caseinate, Malt extract, Skimmed milk powder, Whey powder, Yeast extract, Gluten, Collagen, Gelatin, Elastin, Keratin, and Albumins.

More preferably the cryoprotective agent is a carbonhydrate. Preferred suitable examples of these include the ones selected from the group consisting Pentoses (eg. Ribose, Xylose), Hexoses (eg. fructose, mannose, Sorbose), Disaccharides (eg. Sucrose, Trehalose, Melibiose, Lactulose), Oligosaccharides (eg. Raffinose), Oligofrutoses (eg. Actilight, Fribroloses), Polysaccharides (eg. Maltodextrins, Xanthan Gum, Pectin, Alginate, Microcrystalline cellulose, Dextran, PEG), and Sugar alcohols (Sorbitol, Manitol).

The preferred carbohydrate is a disaccharide preferably Trehalose and more preferably Sucrose.

A preferred mixture of cryoprotective agents is a disaccharide (preferably sucrose) plus a polysaccharide (preferably maltodextrin). Example 4 shows a thermophilic *Lactobacillus acidophilus* culture stabilized with a mixture of sucrose and maltodextrin. Accordingly, for a culture comprising *Lactobacillus acidophilus* it is preferred to use a mixture of a disaccharide (preferably sucrose) and a polysaccharide (preferably maltodextrin) as cryoprotective agents.

Preferably the frozen culture comprises from 2% to 70% of a cryoprotective agent measured as w/w of the frozen material, more preferably from 3% to 50% of a cryoprotective agent measured as w/w of the frozen material, even more preferably from 4% to 40% of a cryoprotective agent measured as w/w of the frozen material and most preferably from 4% to 10% of a cryoprotective agent measured as w/w of the frozen material.

The addition of the cryoprotective agent to the, after fermentation, isolated viable bacteria (biomass) may be done by mixing solid cryoprotective agent with the biomass for e.g. 30 minutes at a suitable temperature. If the cryoprotective agent is e.g. sucrose a suitable temperature may be room temperature. Alternatively a sterile solution of the cryoprotective agent may be mixed with the biomass. For sucrose suitable sterile solutions may be made from a 50% (w/w) sucrose solution. For trehalose suitable sterile solutions may be made from a 40% (w/w) solution.

Use of the Frozen Lactic Acid Bacteria (LAB) Culture

A frozen lactic acid bacteria (LAB) culture as described herein may be used in a process for making a food or feed product according to the art.

A L-culture is preferably used to make cheese with only small holes (cottage cheese) and curdled milk products with low $CO_2$-production.

A LD-culture is preferably used to make cheese with normal hole sizes, curdled milk products (junket) and sour butter.

EXAMPLES

Materials and Methods

Cultures:

F1 DaN, CH N 11 and CH N19 (all commercially available frozen LD-cultures, Chr. Hansen A/S, Denmark).

R-603 (commercially available frozen O-culture, Chr. Hansen A/S, Denmark).

La-5 (commercially available, frozen *Lactobacillus acidophilus* culture, Chr. Hansen A/S, Denmark).

Fermentation Media and Fermentation Conditions:

Medium composition for LD and O-cultures:

The fermentation medium had the following composition: Casein peptone, 30 g/l; Primatone, 30 g/l; soy peptone, 30 g/l; yeast peptone, 15 g/l; $MgSO_4$, 1.5 g/l; Na-ascorbate, 3 g/l; and lactose 50 g/l.

The medium was sterilised by UHT-treatment. The finished medium had a pH of 6.5.

Fermentation Condition for LD and O-Cultures:

The fermentation was performed in a 100 l fermentation tank at 30° C., stirred at 50 rpm. 1% of the culture mentioned above was used as inoculum. The anaerobic fermentation was run with nitrogen in the headspace and a pressure of about 2 bar. The cultures were allowed to acidify to pH 6.2. The pH was subsequently maintained at 6.2 by controlled addition of 13.4 N $NH_4OH$.

When no further base consumption was detected, the respective culture was cooled down to about 10° C.

Following cooling, each of the fermentation broths were concentrated by centrifugation and subsequently frozen as pellets in liquid nitrogen. The pellets were immediately after freezing measured for acidification activity and CFU/g and stored at −50° C. until further analysis.

Media and fermentation condition for *Lactobacillus acidophilus* (La-5):

The culture was grown in MRS broth (Merck, Damstadt, Germany) in a 100 l fermentation tank at 37° C., stirred at 20 rpm. 1% of the culture mentioned above was used as inoculum. The anaerobic fermentation was run with nitrogen in the headspace and a pressure of about 2 bar. The cultures were allowed to acidify to pH 5.5. The pH was subsequently maintained at 5.5 by controlled addition of 13.4 N $NH_4OH$.

When no further base consumption was detected, the respective culture was cooled down to about 10° C.

Following cooling, each of the fermentation broths were concentrated by centrifugation and subsequently frozen as pellets in liquid nitrogen. The pellets were immediately after freezing measured for CFU/g and stored at −50° C. until further analysis.

Acidifying Activity Assay and CFU Analysis:

Frozen culture was inoculated on a 0.01% level in 200 ml sterilized reconstituted skimmed milk (RSM) containing 9.5% solid matter and RSM were incubated at 30° C. for 6 h to permit acidification of the substrate material. The acidification activity was measured as described by Analytical Procedure Q-AM-052, "acidification activity—UHT", Chr. Hansen A/S (Denmark).

CFU analysis was measured and calculated as described by analytical Procedure Q-AM-071, "Enumeration of microorganisms" and Q-AM-022 "Calculation of total count, Chr. Hansen A/S (Denmark) using substrate 1209—LD agar DK-med-rec-123, Chr-Hansen A/S (Denmark) or MRS agar.

Example 1: Stability Study of Frozen LD-Culture of F1 DaN and CH N11 Using Sucrose, Cystain Chloride and Sodium Citrate as Cryoprotective Agents This example describes the stability study with frozen cultures (F-DVS) of F1 DaN and CH N11 formulated with sucrose, cystein chloride and sodium citrate as cryoprotective agents. In all experiments the concentration of cystein chloride and sodium citrate were kept constant per gram concentrated biomass. The concentration of sucrose per gram biomass was varied from 6% (w/w) up to 36% (w/w). All additives were added to the concentrate as solids.

After fermentation, biomass was harvested and concentrated via centrifugation from fermentation broths of CH N 11 and F1 DaN. The cell concentrate of each culture was divided into appropriate portions of 300 gram and formulated as specified in the table 1 below. The additives and concentrates were mixed for 30 minutes and subsequently freezed in liquid nitrogen and stored at −50° C. The frozen culture had a content of viable bacteria of at least $10^{10}$ colony forming units (CFU) per g frozen material. Culture activity in milk was measured the same day as formulated and followed periodically up to one year.

TABLE 1

Formulation procedure for F-DVS of Fl DaN & CH N11.

| Formulation ID | Cell concentrate (g) | Cystein chloride (g) | Sodium Citrate (g) | Sucrose (g) | Sucrose (%) | FL DaN (CFU/g) | CH N11 (CFU/g) |
|---|---|---|---|---|---|---|---|
| F-DVS | 300 | 0.00 | 0.00 | 0 | 0 | 4.0E+10 | 5.0E+10 |
| F-DVS 6% sucrose | 300 | 0.06 | 0.75 | 21 | 6 | 3.7E+10 | 4.7E+10 |
| F-DVS 10% sucrose | 300 | 0.06 | 0.75 | 36 | 10 | 3.6E+10 | 4.5E+10 |
| F-DVS 22% sucrose | 300 | 0.06 | 0.75 | 86 | 22 | 3.1E+10 | 3.9E+10 |
| F-DVS 36% sucrose | 300 | 0.06 | 0.75 | 171 | 36 | 2.5E+10 | 3.2E+10 |

Stability profiles for F-DVS of F1 DaN & CH N11 given as activity versus numbers of days and activity differences compare to day 0 are summarized in FIGS. 1 to 4. It is evident that F-DVS of F1 DaN and CH N 11 free of additives are loosing activity thus stability. The reduction in stability is equal to 0.40 pH units for CH N 11 and 0.60 pH units for F1 DaN after 365 days. All the tested sucrose formulations (6%, 10%, 22% and 36%) seem to have positive effect on the stability. Activity is reduced approx. 0.1 pH unit after 365 days positive effect on the stability. Activity is reduced approx. 0.1 pH unit after 365 days of storage at −55° C.

Example 2: Stability Study of Frozen LD-Culture of F1 DaN, CH N11 & CH N19 Using Sucrose and Trehalose as Cryoprotective Agents This example describes the stability study with frozen cultures of F1 DaN and CH N11 and CH N 19 formulated with sucrose and trehalose as cryoprotective agents. The concentration of sucrose per gram biomass was varied from 6% (w/w) up to 10% (w/w). Trehalose was only tested on a 5 (w/w) level. All sucrose concentrations were prepared from a 50% (w/w) sucrose solution added to the biomass. The trehalose concentration was prepared from a 40% (w/w) solution.

After fermentation, biomass was harvested and concentrated via centrifugation from fermentation broths of F1 DaN, CH N 11 and CH N19. The cell concentrate of each culture was divided into appropriate portions of 300 gram and formulated as specified in the table 2 below. The additives and concentrates were mixed for 30 minutes and subsequently freezed in liquid nitrogen and stored at −50° C. The frozen culture had a content of viable bacteria of at least $10^{10}$ colony forming units (CFU) per g frozen material. Culture activity in milk was measured the same day as formulated and followed periodically up to 70 days.

TABLE 2

Formulation procedure for F-DVS of Fl DaN, CH N 11 & CH N19 using sucrose and trehalose as cryoprotective agents

| Formulation ID | Cell concentrate (g) | Additive solution (g) | Final additive conc. (% Sucrose) | Fl DaN CFU/g | CH N19 CFU/g |
|---|---|---|---|---|---|
| F-DVS | 300 | 0 | 0 | 3.0E+10 | 4.0E+10 |
| F-DVS/07G | 300 | 43 | 6 | 2.6E+10 | 3.5E+10 |
| F-DVS 5% Trehalose | 300 | 43 | 5 | 2.6E+10 | 3.5E+10 |

TABLE 2-continued

Formulation procedure for F-DVS of Fl DaN, CH N 11 & CH N19 using sucrose and trehalose as cryoprotective agents

| Formulation ID | Cell concentrate (g) | Additive solution (g) | Final additive conc. (% Sucrose) | Fl DaN CFU/g | CH N19 CFU/g |
|---|---|---|---|---|---|
| F-DVS 3% Sucrose | 300 | 19 | 3 | 2.8E+10 | 3.8E+10 |
| F-DVS 5% Sucrose | 300 | 34 | 5 | 2.7E+10 | 3.6E+10 |
| F-DVS 6% Sucrose | 300 | 42 | 6 | 2.6E+10 | 3.5E+10 |
| F-DVS 8% Sucrose | 300 | 57 | 8 | 2.5E+10 | 3.4E+10 |
| F-DVS 9% Sucrose | 300 | 66 | 9 | 2.5E+10 | 3.3E+10 |
| F-DVS 10% Sucrose | 300 | 75 | 10 | 2.4E+10 | 3.2E+10 |
| F-DVS 13% Sucrose | 300 | 105 | 13 | 2.2E+10 | 3.0E+10 |

Stability profiles for F-DVS of F1 DaN, CH N11 & CH N19 using sucrose and trehalose as cryoprotective agents are summarized in FIGS. 5 to 10.

All reference cultures have lost activity (F1 DaN: 0.3 pH units after 65 days at −50° C.; CH N 11: 0.17 pH units after 60 days at −50° C.; CH N 19: 0.25 pH units after 70 days at −50° C.). All the tested formulations reduce the activity loss compare to the reference cultures. Furthermore, it is difficult to conclude which sucrose concentration is optimum with regard to stability.

From the stability profiles of F1 DaN and CH N19 it can be observed that the reference and the tested sucrose formulations have an initial lost of activity within the first 1-3 weeks of storage. Hereafter, all the sucrose formulated concentrates show a constant stability profile. F1 DaN shows a higher initial loss than CH N19. However, no initial loss of activity could be observed from the stability profiles of all the tested formulations of CH N11.

Example 3: Stability Study of Frozen O-Culture of R-603

Figure 1:
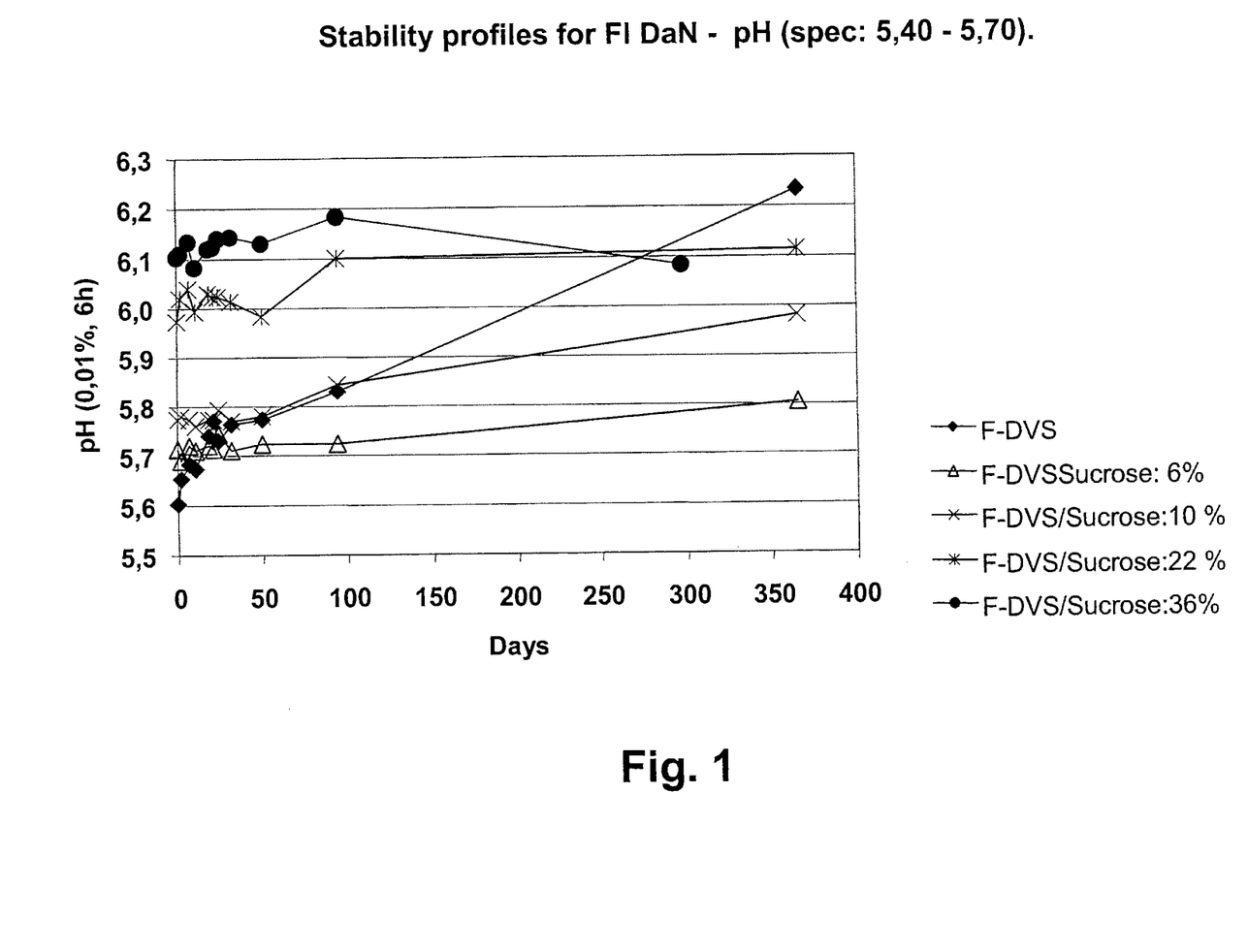
FIGS. 1 to 4: Stability profiles for F-DVS of F1 DaN & CH N11. For further details see working Example 1.
Figure 2:
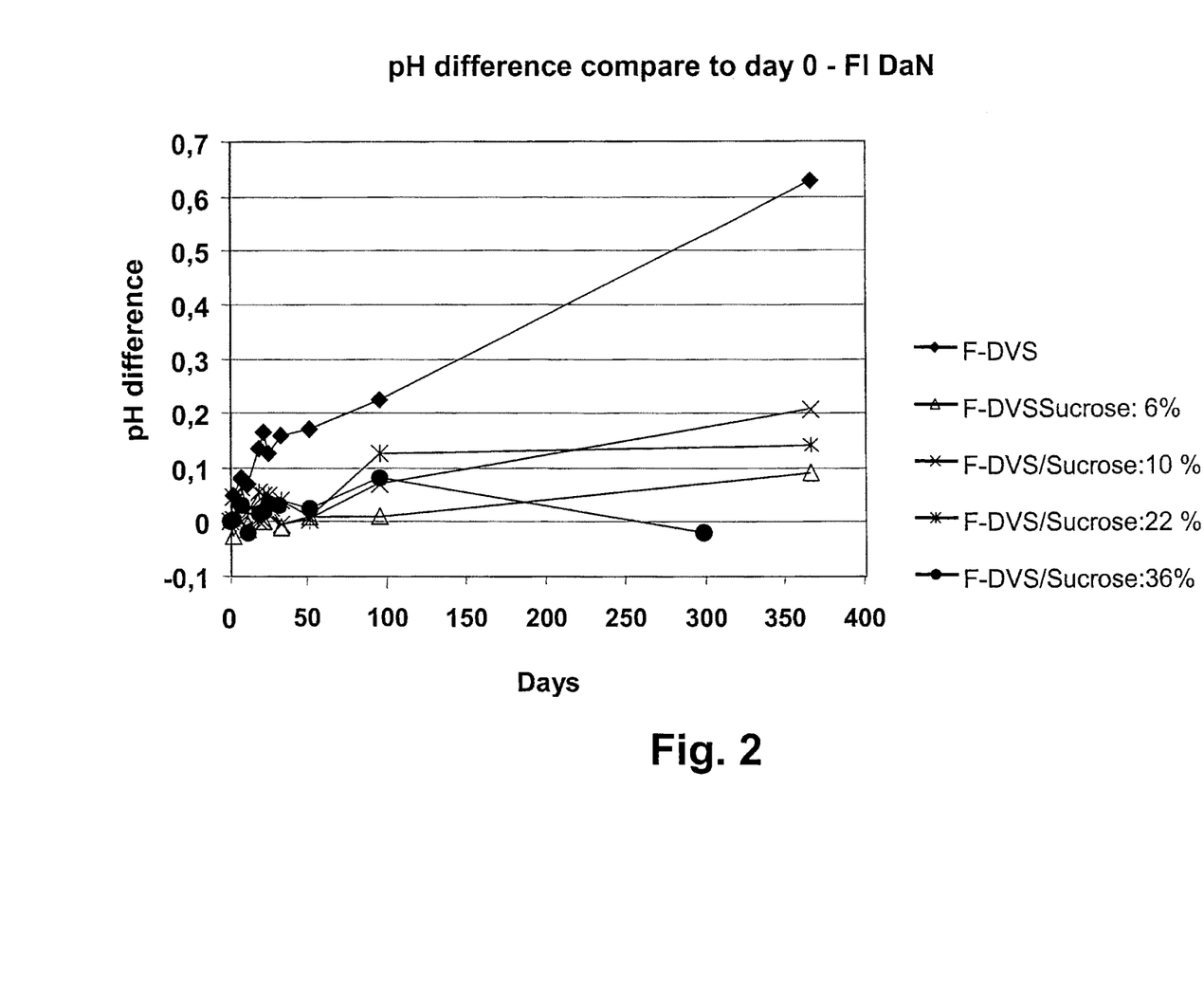
Figure 3:
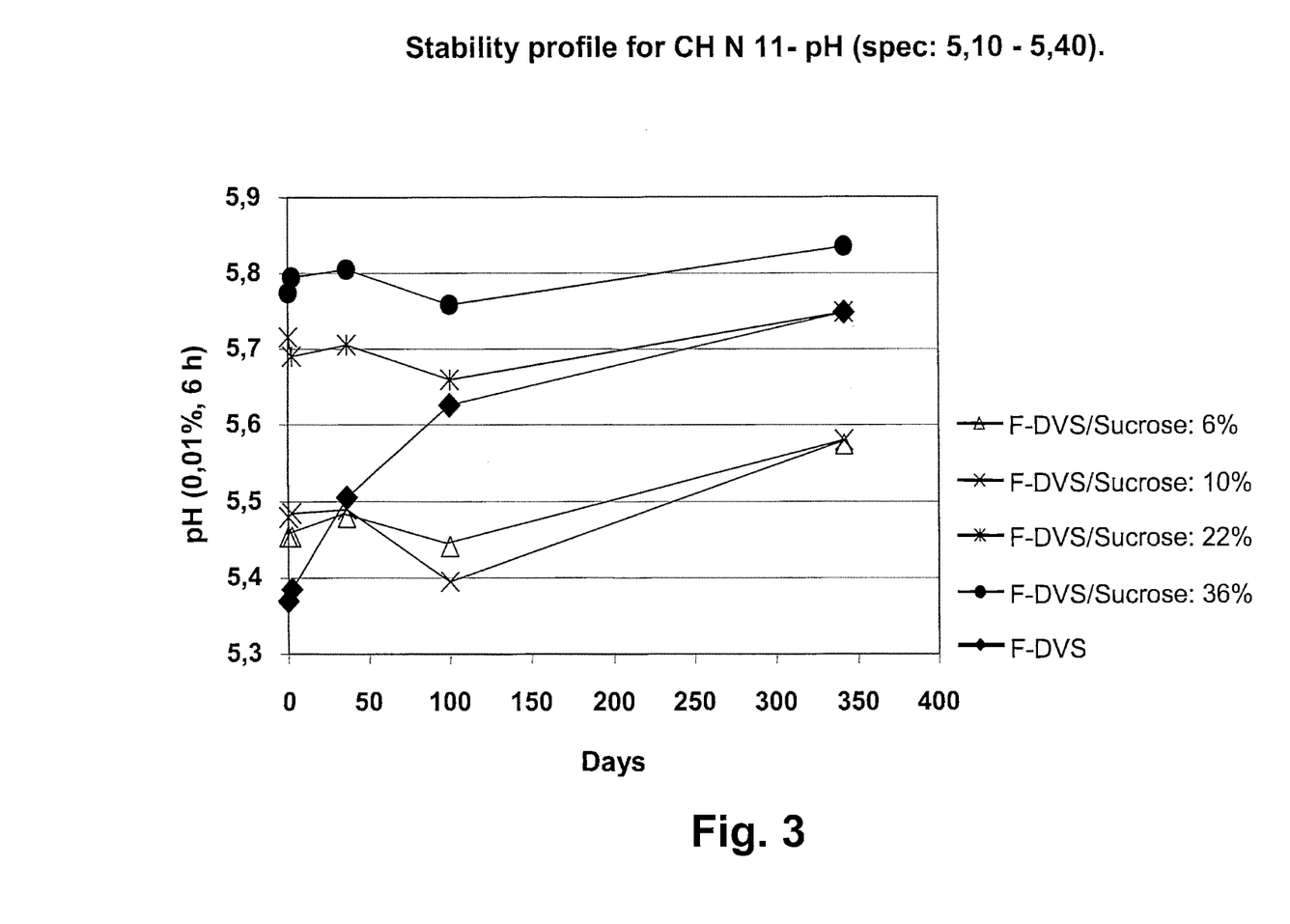
Figure 4:
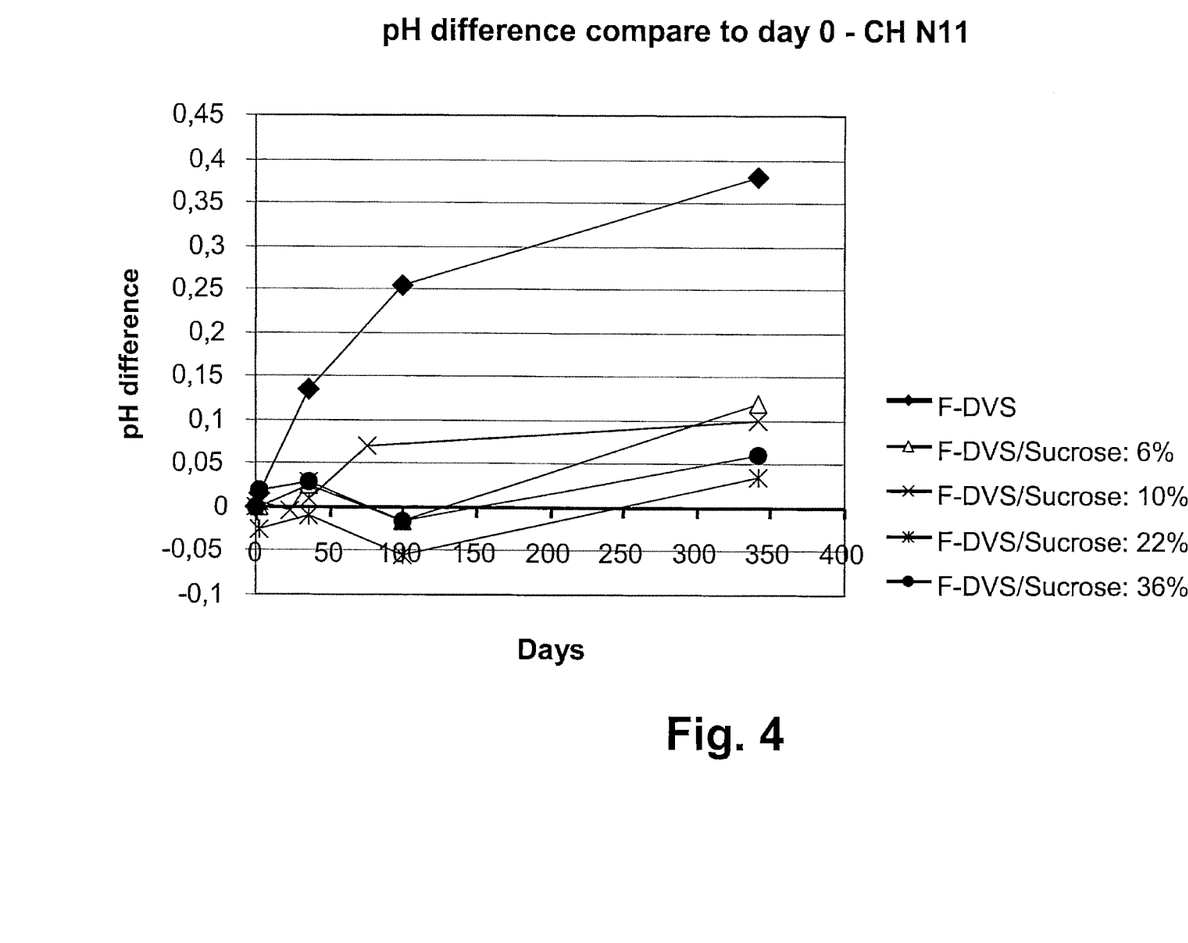
Figure 5:
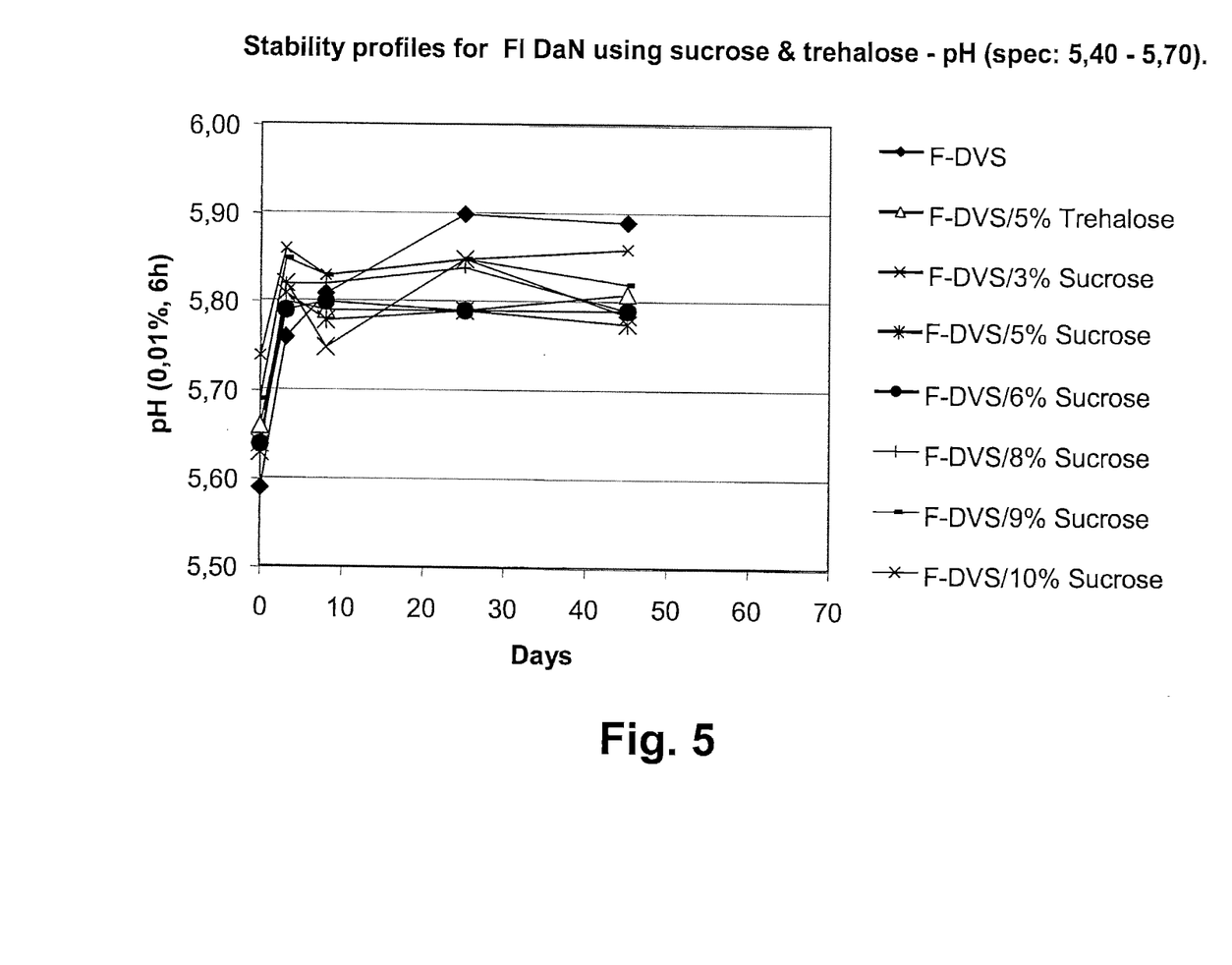
FIGS. 5 to 10: Stability profiles for F-DVS of F1 DaN, CH N11 & CH N19. For further details see working Example 2.
Figure 6:
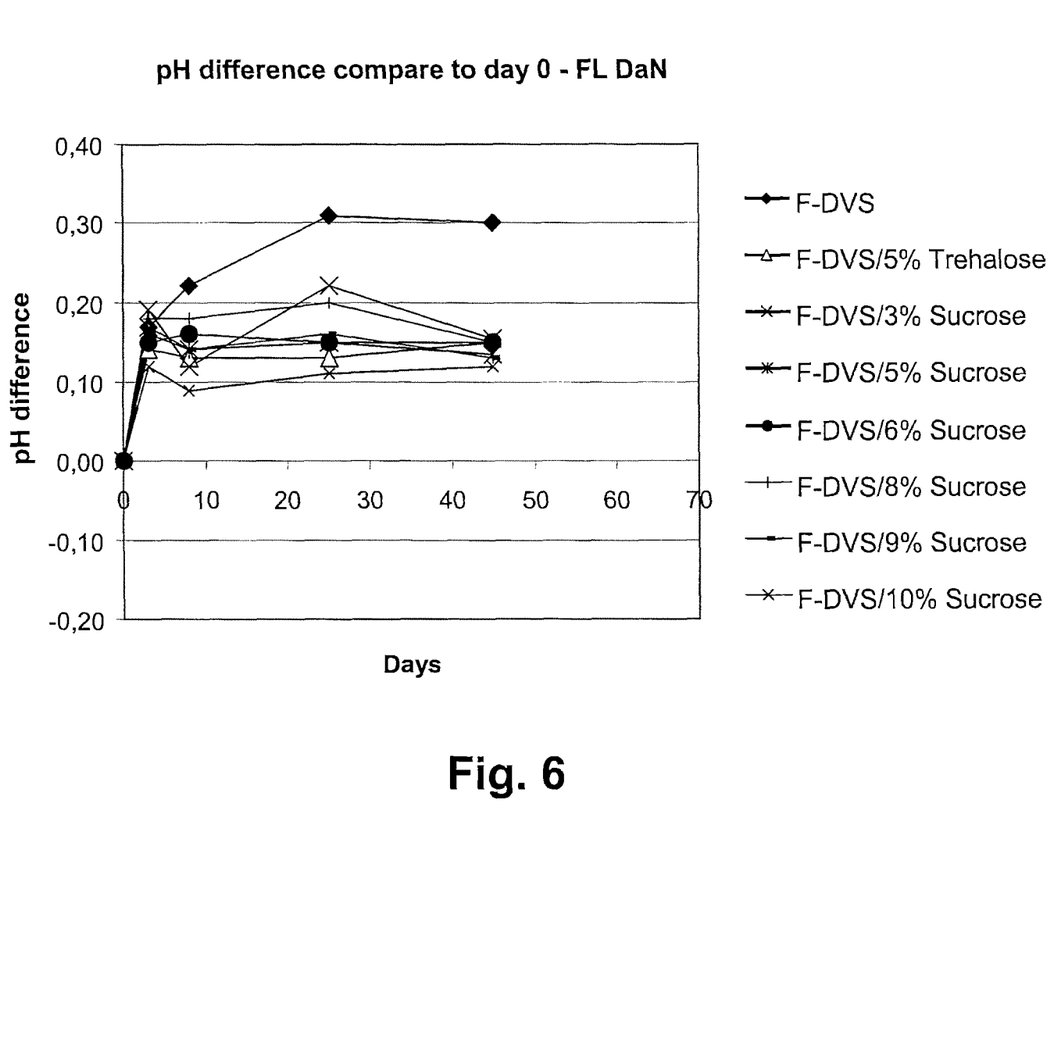
Figure 7:
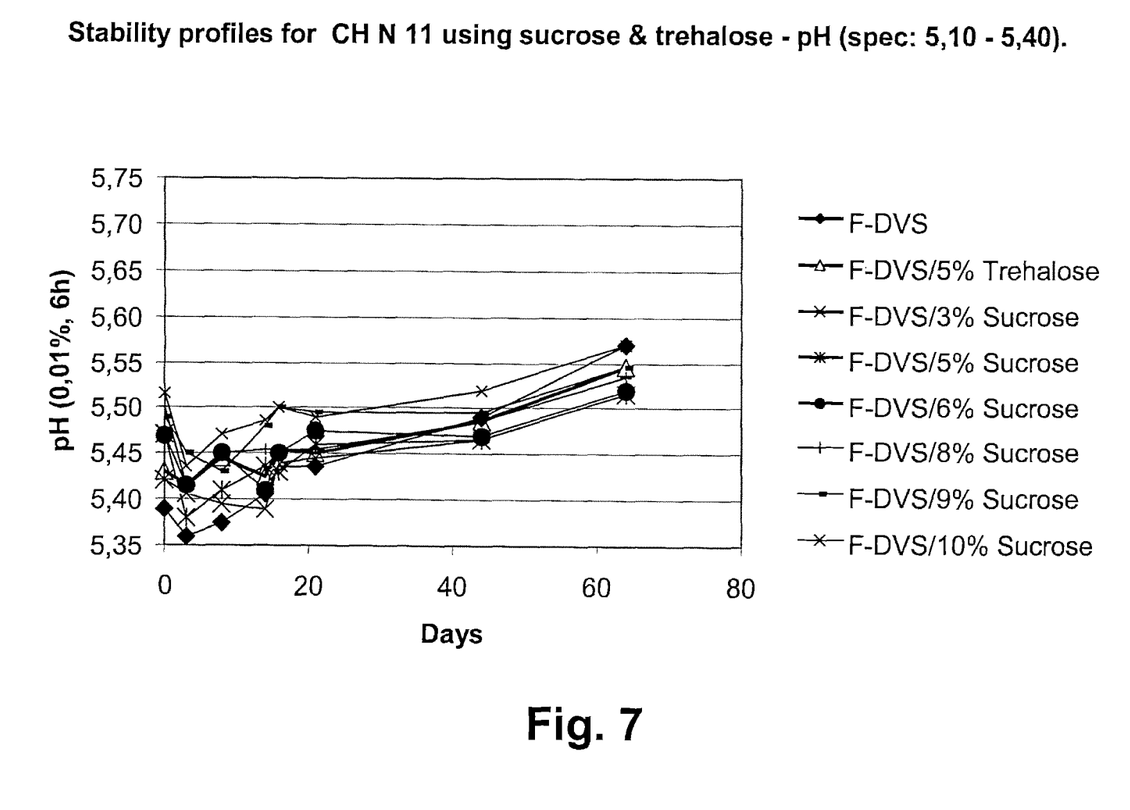
Figure 8:
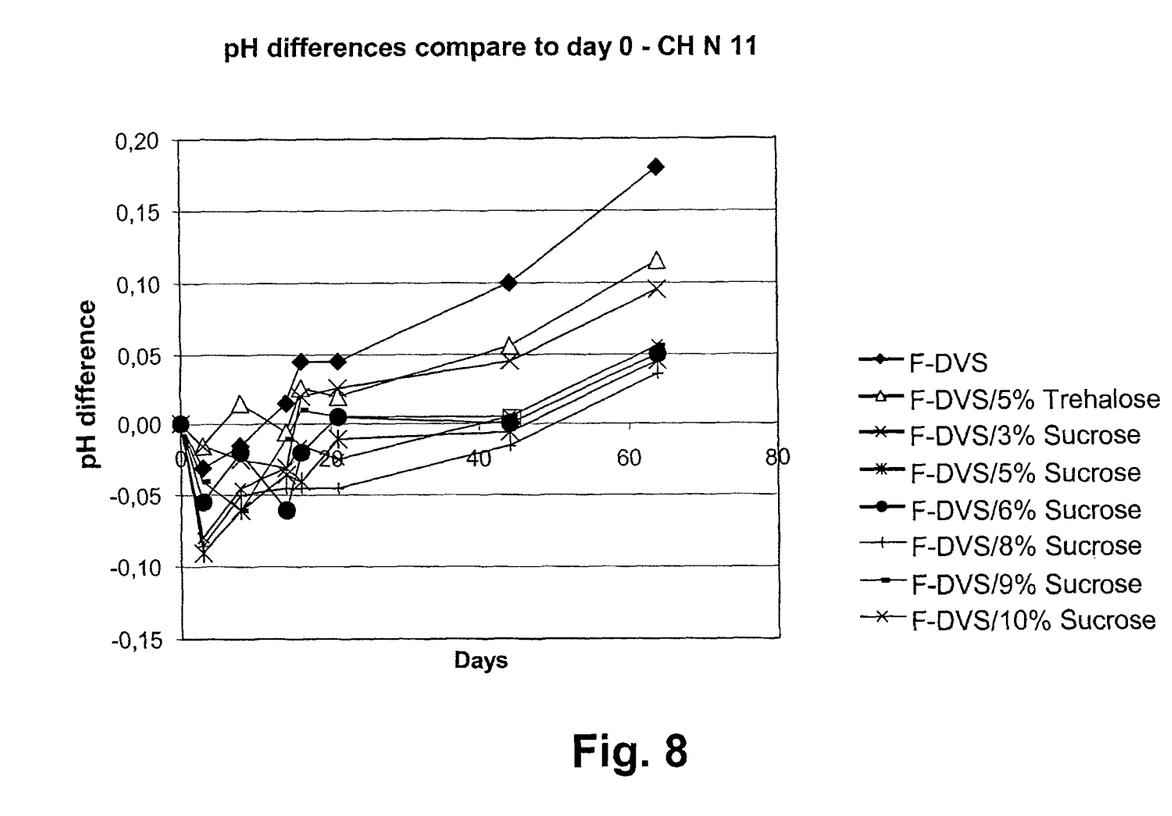
Figure 9:
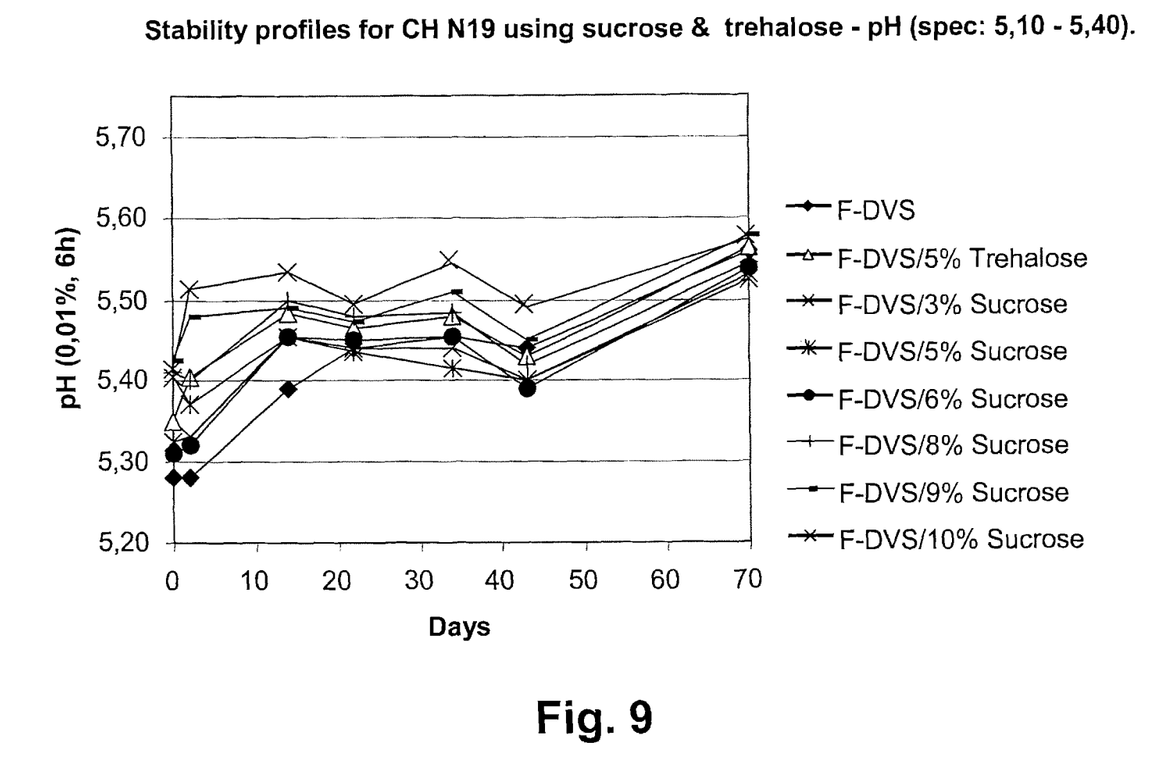
Figure 10:
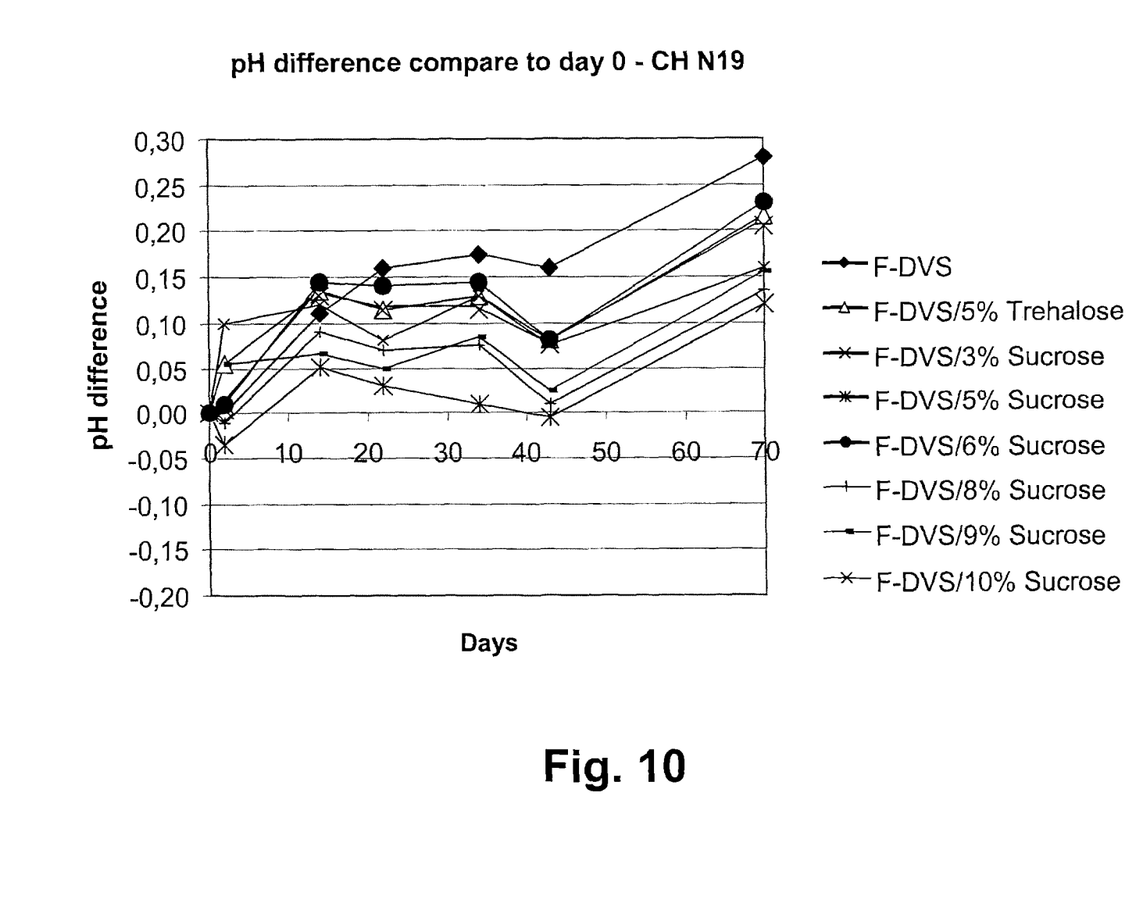
Figure 11:
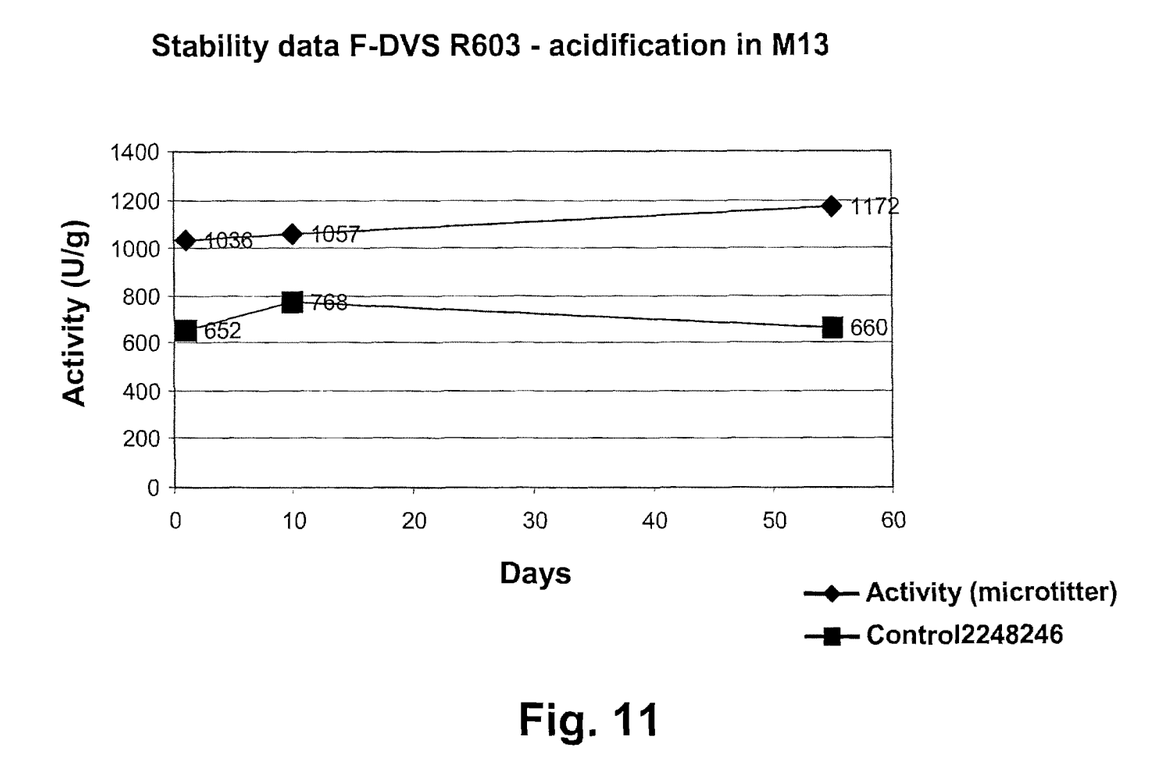
FIG. 11: Stability profiles for R603. For further details see working Example 3.

Initial loss of activity within the first 1-3 weeks has so far not been seen for any of Chr. Hansen A/5 commercial available O-cultures (*Lactococcus lactis* subsp. *cremoris* & *Lactococcus lactis* subsp. *lactis*). Stability profiles for R603 followed up to 35 days and analyzed for acidification in M17 media is summarized in FIG. 11.

Example 4: Stability Study of Frozen *Lactobacilus acidophislus* (La-5)

This example describes the stability study with frozen cultures of *Lactobacillus acidophilus* formulated with sucrose or sucrose and maltodextrine as cryoprotective agents. The concentration of sucrose per gram biomass was 32% (w/w). Sucrose and maltodextrine were tested at 16%/16% (w/w) level.

After fermentation, biomass was harvested and concentrated by centrifugation. The cell concentrate was divided into appropriate portions of 300 gram and formulated. The additives and concentrates were mixed for 30 minutes and subsequently freezed in liquid nitrogen and stored at −20, −50 or −80° C. The stability was measured as colony-forming units (CFU) per g frozen material on MRS agar 37° C. (72 hours).

TABLE 3

*Lactobacillus acidophilus* stored at different temperatures.
Storage stability is measured as CFU/g after 6, 13, and 68 days

| Days | Temp = −20° C. | Temp = −50° C. | Temp = −80° C. | +32% Sucrose at −20° C. |
|---|---|---|---|---|
| 0  | 4.35E+10 | 4.35E+10 | 4.35E+10 | 3.82E+10 |
| 6  | 3.14E+10 | 4.87E+10 | 4.77E+10 | 2.61E+10 |
| 13 | 2.75E+10 | 4.37E+10 | 4.61E+10 | 2.50E+10 |
| 68 | 6.52E+09 | 4.15E+10 | 4.14E+10 | 2.51E+10 |

TABLE 4

*Lactobacillus acidophilus* stored at −20° C. without additives and with 32% sucrose or with 16% sucrose + 16% maltodextrine.

| Days | without additives | 32% sucrose | 16% sucrose + 16% maltodextrine |
|---|---|---|---|
| 0  | 2.81E+10 | 3.02E+10 | 3.82E+10 |
| 7  | 1.81E+10 | 1.99E+10 | 2.97E+10 |
| 14 | 1.11E+10 | 1.56E+10 | 2.04E+10 |
| 21 | out of range | 1.98E+10 | 2.93E+10 |
| 54 | 8.60E+09 | 1.53E+10 | 2.54E+10 |

*Lactobacillus acidophilus* seems storage stable at −50 and −80° C., but the viability is declining if the culture is stored at −20° C. By use of additives; sucrose or sucrose and maltodextrine—it is possible to improve the stability of the culture at −20° C.

REFERENCES

EP 259739 A1, Miles Laboratories, 16 Mar. 1988

F. J. Chavarri et al, "Cryoprotective agents for frozen concentrated starters from non-bitter *Streptococcus Lactis* strains", *Biotechnology letters*, vol 10, 1, 11-16 (1988)

R. Cárcoba et al., "Influence of cryoprotectants on the viability and acidifying activity of frozen and freeze-dried cells of the novel starter strain *Lactococcus lactis* subsp. *lactis* CECT 5180", *Eur Food Res Technol* (2000) 211, 433-437

WO 00/39281, Chr. Hansen A/S, 6 Jul. 2000

The invention claimed is:

1. A frozen lactic acid bacteria culture comprising:
   a mixture of mesophilic lactic acid bacteria that (a) have an optimum growth temperature of about 30° C. and (b) are capable of utilizing sucrose, and
   from 0.5% to 80% w/w of at least one cryoprotective agent,
   wherein the frozen culture is not freeze-dried and has a weight of at least 50 grams and comprises at least $10^9$ colony forming units of viable bacteria per gram.

2. The frozen culture of claim 1, wherein the culture is a LD-culture comprising *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

3. The frozen culture of claim 1, wherein the culture is an L-culture.

4. The frozen culture of claim 1, further comprising a thermophilic *Streptococcus thermophilus* bacterium.

5. The frozen culture of claim 1, further comprising a thermophilic *Lactobacillus acidophilus* bacterium.

6. The frozen culture of claim 1, wherein the at least one cryoprotective agent comprises a carbohydrate.

7. The frozen culture of claim 1, wherein the at least one cryoprotective agent comprises a disaccharide.

8. The frozen culture of claim 1, wherein the at least one cryoprotective agent comprises at least one of trehalose and sucrose.

9. The frozen culture of claim 1, wherein the at least one cryoprotective agent comprises a mixture of a disaccharide and a polysaccharide.

10. The frozen culture of claim 9, wherein the disaccharide comprises sucrose and the polysaccharide comprises maltodextrin.

11. The frozen culture of claim 1, wherein the at least one cryoprotective agent is selected from the group consisting of a protein, a protein hydrolysate, and an amino acid.

12. The frozen culture of claim 1, wherein the frozen culture comprises from 3% to 50% w/w of the at least one cryoprotective agent.

13. The frozen culture of claim 1, wherein the frozen culture comprises from 4% to 10% w/w of the at least one cryoprotective agent.

14. A food or feed product made using the frozen culture of claim 1.

15. A method of making a food or feed product, wherein the method comprises adding the frozen culture of claim 1 to a food or feed material.

16. A method for making a frozen lactic acid bacteria culture comprising:
   (i) adding at least one cryoprotective agent to a mixture of mesophilic lactic acid bacteria that (a) have an optimum growth temperature of about 30° C. and (b) are capable of utilizing sucrose; and then
   (ii) freezing the culture,
   wherein the frozen culture is not freeze-dried and has a weight of at least 50 grams and comprises (a) at least $10^9$ colony forming units viable bacteria per gram and (b) from 0.5% to 80% w/w of the at least one cryoprotective agent.

17. The method of claim 16, wherein the culture is a LD-culture comprising *Lactococcus lactis* subsp. *lactis, Lactococcus lactis* subsp. *cremoris, Lactococcus lactis* subsp. *lactis* biovar. *diacetylactis* and *Leuconostoc mesenteroides* subsp. *cremoris*.

18. The method of claim 16, wherein the frozen mixture comprises from 3% to 50% w/w of the at least one cryoprotective agent.

19. The method of claim 16, wherein the frozen culture comprises from 4% to 10% w/w of the at least one cryoprotective agent.

* * * * *